United States Patent
Nadachi et al.

(10) Patent No.: US 6,605,297 B2
(45) Date of Patent: Aug. 12, 2003

(54) SUBSTANCES HAVING ANTIOBESE AND VISCERAL FAT-REDUCING FUNCTIONS AND UTILIZATION THEREOF

(75) Inventors: Yoshitaka Nadachi, Tokyo (JP); Kenji Koga, Tokyo (JP); Masayuki Mizuno, Tokyo (JP)

(73) Assignee: Janiftec, Inc., Tokyo (JP)

( * ) Notice: Subject to any disclaimer, the term of this patent is extended or adjusted under 35 U.S.C. 154(b) by 0 days.

(21) Appl. No.: 10/319,547

(22) Filed: Dec. 16, 2002

(65) Prior Publication Data

US 2003/0119907 A1 Jun. 26, 2003

Related U.S. Application Data (62) Division of application No. 09/786,124, filed as application No. PCT/JP99/04734 on Sep. 1, 1999, now abandoned.

(30) Foreign Application Priority Data

Sep. 1, 1998 (JP) .......................................... 10-262295
Aug. 31, 1999 (JP) .......................................... 11-245357

(51) Int. Cl.$^7$ .............................................. A61K 47/00
(52) U.S. Cl. ..................... 424/439; 424/400; 424/78.01
(58) Field of Search ............................... 424/400, 439, 424/78.01

(56) References Cited

FOREIGN PATENT DOCUMENTS

GB          1108898          4/1968

OTHER PUBLICATIONS

G. Rosenblat, et al., "Inhibition of Bacterial Urease by Autoxidation of Furan C–18 Fatty Acid Methyl Ester Products", J. Am. Oil. Chem. Soc., May 1993, vol. 70, No. 50, pp. 501–505.

S. Banni et al., "Detection of Conjugated Diene Isomers of Linoleic Acid in Liver Lipids of Rats Fed a Choline–Devoid Diet Indicates that the Diet does not cause Lipoperoxidation." J. Nutr. Biochem., May 1995, vol. 6, pp. 281–289 (especially, Table 3).

M. L. Wise et al., "Characterization of the Substrate Binding Site of Polyenoic Fatty Acid Isomerase, a Novel Enzyme from the Marine Alga Ptilota Filicina." Biochemistry, 1997, vol. 36, pp. 2985–2992 (Abstract, Schemes 1,2).

*Primary Examiner*—Thurman K. Page
*Assistant Examiner*—Charesse Evans
(74) *Attorney, Agent, or Firm*—Oblon, Spivak, McClelland, Maier & Neustadt, P.C.

(57) ABSTRACT

The present invention is substances comprising coupling isomerized highly unsaturated fatty acids and/or their derivatives having an activity of specifically promoting the uncoupling respiration of mitochondria (MC) and proton leak in the MC inner membrane in cells of the main tissues producing nonshivering thermogenesis (nST), skeletal muscles, white adipose tissue (WAT) and brown adipose tissue (BAT).

16 Claims, 1 Drawing Sheet

UCP1

UCP2

UCP3

GAPDH

SUBSTANCES HAVING ANTIOBESE AND VISCERAL FAT-REDUCING FUNCTIONS AND UTILIZATION THEREOF

CROSS-REFERNCE TO RELATED APPLICATIONS

The present application is a Divisional Application of U.S. Ser. No. 09/786,124 filed on Mar. 26, 2001, now abandoned; which is a 371 application PCT/JP99/04734 filed on Sep. 1, 1999.

TECHNICAL FIELD

The present invention is novel substances with the function of specifically accelerating uncoupled respiration and proton leak of the inner membrane of mitochondria which are induced by uncoupling proteins (UCP) (hereafter referred to as proton leak), in the functions of mitochondoria (hereafter referred to as MC), which is infracellular organelles performing the energy metabolism (respiration) using as the substrate fatty acids and pyruvic acid. In further detail, the present invention relates to the novel substances comprising a coupling isomerized highly unsaturated fatty acid and/or its derivative with the function of specifically promoting proton leak of the MC of mammals, including humans, etc., anti-obese (inhibiting the accumulation of visceral fat (particularly mesenteric fat) (hereafter referred to as visceral fat)) and visceral (particularly mesenteric (hereafter referred to as visceral) fat-reducing agents comprising the above-mentioned substance as the active ingredient, food products having anti-obese (inhibiting the accumulation of visceral fat) and visceral fat-reducing activities comprising the above-mentioned substance as the active ingredient, and feed having anti-obese (inhibiting accumulation of visceral fat) and visceral fat-reducing activities comprising the above-mentioned substance as the active ingredient.

BACKGROUND ART

The energy metabolism-regulating system in vivo consists of the food ingestion-regulating system and energy consumption-regulating system. The purpose of the present invention is to realize inhibition of accumulation of visceral fat and reduction thereof, which is considered as a multiple risk factor for lifestyle disease, in relation to joint-control of the energy-regulating system.

The energy consumption-regulating system is classified into energy consumption used for basal metabolism in order to sustain life and other energy consumption. The main energy consumption under the latter category is nonshivering thermogenesis (hereafter nST) and its functional significance is maintenance of body temperature, during exposure to cold, when waking from hibernation, etc., and to prevent obesity and impaired glycolipid metabolism due to consumption of energy from overeating, etc. Uncoupled respiration by mitochondria (MC) and proton leak of the inner membrane of MC, that is, the participation of the electron transport system of the respiration chain of the cells and ATP synthesis, are important to the mode by which nST is induced. The details are given below: ATP is essential for maintaining cell function, and in the cells, fatty acids and the pyruvic acid produced by the glycolysis system of cytoplasm are transported to MC and are oxidized to produce acetyl CoA. This acetyl CoA is oxidized by the citric acid circuit, with carbon dioxide and NADH being produced during this oxidation process and high-energy electrons further being produced from the NADH. The high-energy electrons bond with molecular oxygen in the respiration chain (electron transport system) of the inner membrane of MC to release energy. This energy pumps protons from the matrix through the inner MC to the intermembrane space.

As a result, an electrochemical gradient of protons is formed on both sides of the inner membrane. Then, when the protons of the intermembrane space return to the matrix in accordance with this gradient, ATP synthetase bound to the membrane is actuated to produce ATP from ADP+Pi.

The speed of the electron transport system of the respiration chain is regulated in order to maintain a constant ratio of ATP and ADP in vivo in accordance with the status thereof. If there is an increase in ATP consumption, the speed of electron transport will also become faster and as a result, it will be necessary to feed substrate. When strenuously moving, fatty acids and sugar are oxidized at a speed that is 5-times to 10-times that when resting.

The fat-soluble weak acid 2,4-dinitrophenol (2,4-DNP) acts as a proton ionophore to form a path through which protons other than ATP synthetase will flow through the inner membrane of the MC. Thus, the electrochemical gradient of the protons that was produced by the respiration chain of the inner membrane is consumed and ATP is not synthesized. That is, 2,4-DNP uncouples ATP synthesis with the electron transport system of the respiration chain and therefore acts as an uncoupling agent. Since ATP is not synthesized, electron transport of the respiration chain proceeds at the maximum speed at which feeding of substrate is allowed (Hosoda et al., Mebio, 14 (11), 30–31 (1997)).

A specific protein, uncoupling protein 1 (UCP-1), which uncouples ATP synthesis with the respiration chain electron transport system within the MC of brown adipocytes (BA), is a protein with a molecular weight of 32 kD consisting of approximately 300 amino acids that is present in brown adipose tissue (BAT). UCP-1 consists of 3 repeating domains consisting of approximately 100 amino acids and has 2 membrane-perforation sites in each domain, for a total of 6 sites.

These membrane perforation sites form a channel. UCP-1 is the carrier that transports protons and has the ability to be freely permeated by protons via this proton channel to release heat in accordance with the electrochemical gradient. This becomes nST. There is a reduction in ATP synthesis with uncoupling, and respiration inside the MC is activated in order to keep the ATP and ADP ratio constant and as a result, large amounts of fats and sugar are oxidized to generate heat.

Regulation of the functions of UCP-1 is performed from both aspects of the amount expressed and activity thereof. That is, the noradrenaline secreted from the sympathetic nerve terminals activates adenylic acid cyclase via the β-adrenaline receptors (β-AR) on the cell membrane to elevate intracellular cAMP concentrations.

The cAMP breaks down neutral fats via activation of protein kinase A (PKA) and activation of hormone-sensitive lipase (HSL) to produce free fatty acids (FFA). These FFA bind with UCP-1 to open the protein channels that were closed and act as a heat-production substrate. On the other hand, the amount of UCP-1 expressed is regulated mainly on the endonuclear gene transcription level, and UCP-1 gene expression is increased by elevation of cAMP concentrations (Saito et al., Saishin Igaku, 52, 1095–1096 (1997)).

UCP-1 is physiologically significant in that it is important in body temperature maintaining, during exposure to cold, etc., and research using transgenic mice has also made it clear that it participates in the prevention of obesity. That UCP-1 participates in the development, progression and persistence of obesity is indicated by the fact that there is a reduction in UCP-1 expression with various obesity models. Furthermore, it is confirmed that obesity develops without overeating in BAT-reduced transgenic mice (Lowell, B. B et al., Nature, 366, 740–742 (1993)). On the other hand, a reduction in body fat when large amounts of UCP-1 are expressed has beep ascertained in mice forced to express UCP-1 by insertion of the promoter of adipocyte-specific gene aP2 (Kopecky J. et al., J Clin Invest, 96, 2914–2923 (1995)).

Nevertheless, there is the idea that BAT is present in adult humans in only very small amounts and BAT-specific UCP-1 hardly has physiological significance.

On the other hand, there is also the opinion that the idea that the physiological significance of this BAT applies not only to laboratory animals, but also adult humans is supported from the following several points (Teruo Kawada, private message).

(1) As a result if it becoming possible to determine the amount of UCP, it is known that BAT is present perinephric and intra-abdominal in all those assayed, from neonates (1 day) to elderly (86 years), even in humans.

(2) Although more is found in children up to 15 years of age, approximately 50 g are present in adults, and the reduction in this activity may induce a body weight increase of 25 kg in 1 years.

(3) As with adult humans, BAT is converted to white cells in adult dogs and BAT is hardly detected, however, when β-3 adrenalin receptor-acting drugs are chronically administered, the immature or undifferentiated brown adipose tissue is activated and UCP and its genetic mRNA are expressed as differentiated BA.

Approximately 20 to 40% of intracellular energy consumption appears to be produced by proton leak of the MC inner membrane. Moreover, the majority of nST appears to be produced in the skeletal muscles and white adipose tissue (WAT) in adult humans and other animals with little BAT. Based on the above-mentioned facts, it has been estimated that UCP is present in tissue other than BAT. cDNA cloning of UCP-2 was reported in succession by 2 groups in 1997 (Fleury, C. et al., Nature Genet, 15, 269–272 (1997): Gimeno, R. et al., Diabetes 46, 900–906 (1997)). Human UCP-2 shows 59% homology with human UCP-1, and as with UCP-1, forms a channel with 6 sites for penetration trough membrane.

Moreover, it has a purine nucleotide-binding site. UCP-2 differs from UCP-1 in that it is widely expressed in systemic tissue and is found in particularly high concentrations in the lung and pancreas, and expression is also detected in the heart, liver, brain, kidneys, testicles, WAT, BAT and skeletal muscles. Moreover, accelerated expression of UCP-2 gene in fat tissue around seminal vesicles in high fat-loaded mice.

Even though skeletal muscles are the main nST tissue, the concentration of UCP-2 gene expressed in skeletal muscle is relatively low in contrast to the relatively high concentrations in WAT and it is estimated that UCP other than UCP-2 is present in skeletal muscles. Novel UCP consisting of 308 amino acids was first isolated and identified in the skeletal muscles of rats and shows 57% and 72% homology with rat UCP-1 and UCP-2 respectively. Moreover, gene expression in rat tissue was detected in particularly high concentrations in skeletal muscles, intermediate concentrations in BAT, and low concentrations in WAT and the heart (Matsuda, J., et al., submitted).

Next, cDNA cloning of UCP-3, which is expressed in high concentrations in human skeletal muscles, was reported by 2 groups (Boss, O. et al., FEBS Lett, 408, 39–42 (1997); Vidal-Puig, A. et al., Biochem Biophys Res Commun, 235, 79–82 (1997)). It showed 87% homology with the previous rat novel UCP (Hosoda et al., Mebio, 14, (11), 33–34 (1997)).

Isolation and identification of various uncoupling proteins and assessment of their functions, as well as inquiry into methods of accelerating their expression, have been promoted by newly confirming that UCP genes different from those of conventional genes are expressed in skeletal muscles and WAT, the main nST tissues, and epoch-making breakthroughs are expected in terms of anti-obesity in adult humans.

The excess energy in vivo is stored, first predominantly as visceral fats (particularly mesenteric fat), and this visceral fat is more readily mobilized than fats in other parts of the body (particularly subcutaneous fats) to quickly break down and be consumed. This visceral fat (obesity) is regarded as a multiple risk factor for the occurrence of lifestyle-related disease (adult disease). The reason for this is that the secreted fatty acids from the white adipocytes (WA) of WAT flow directly into the liver and accelerate insulin resistance and fat synthesis and as a result, induce sugar resistance anomalies, high blood pressure and hyperlipidemia, and these are eventually complicated by the development of arteriosclerosis.

The above-mentioned is the reason why inhibition of the accumulation of this visceral fat and reducing accumulation of visceral fat is expected to contribute considerably to the prevention and treatment of lifestyle-related illness in adult humans.

SUMMARY OF THE INVENTION

The present invention presents substances having anti-obese and accumulated visceral fat-reducing activities and a method of using the same.

The present invention is substances comprising coupling isomerized highly unsaturated fatty acids and/or their derivatives having an activity of specifically promoting the uncoupling respiration of mitochondria (MC) and proton leak in the MC inner membrane in cells of the main tissues producing nonshivering thermogenesis (nST), skeletal muscles, white adipose tissue (WAT), brown adipose tissue (BAT), etc. in mammals including humans, and birds, anti-obese (inhibiting the accumulation of visceral fat (particularly mesenteric fat)) and visceral (particularly mesenteric) fat-reducing agents containing the above substances as the active ingredient, food products having anti-obese (inhibiting the accumulation of visceral fat (particularly mesenteric fat)) and visceral (particularly mesenteric) fat-reducing activities comprising as their active ingredient the above-mentioned substances, and feed having anti-obese (inhibiting the accumulation of visceral fat (particularly mesenteric fat)) and visceral (particularly mesenteric) fat-reducing activities comprising as their active ingredient the above-mentioned substances.

The above-mentioned substance obtained by the present invention has the effect of specifically accelerating uncoupled respiration of MC and proton leak of the MC inner membrane in BA, cells comprising mitochondria and WA, etc., such as skeletal muscles, WAT, and BAT, etc., which are the main tissues of nST, among the cells of body tissue of mammals, including humans, and birds.

DISCLOSURE OF THE INVENTION

In order to realize inhibition of accumulation of visceral fat (particularly mesenteric fat), which is a multiple risk factor for lifestyle-related disease in adult humans (adult disease), and reducing of accumulated visceral fat, the present invention creates means for accelerating the functions of UCP subtypes UCP-3 and UCP-2, the presence of which has recently been confirmed on a genetic level and which are expressed to high concentrations in skeletal muscles and WAT, the main tissues involved in nST (nonshivering thermogenesis), in addition to the conventional acceleration of MC proton leak of the relatively little BAT as tissue involved in nST, when laying the basic foundation for promoting nST in the energy consumption-regulating system in vivo and thereby dramatically improve efficiency of the same.

The main object of this invention is to newly introduce various mRNA assay systems to UCP subtypes and study mRNA of all subtypes using the BAT of rats reared on coupling isomerized fish oil, emphasizing the fact that UCP subtype mRNA is expressed in all BAT and the fact that coupled isomerized fish oil accelerates expression of UCP in BAT.

That is, the object of the present invention is to present a substance comprising coupling isomerized highly unsaturated fatty acids and/or derivatives of the same having the function of increasing nST function by specifically accelerating proton leak in the mitochondria of skeletal tissues and WAT, which are the main tissues involved in nST, and BAT, which has extremely strong activity per unit although the amount of tissue is small, belonging to the main in vivo energy consumption-regulating system in mammals, including humans, anti-obese (inhibiting accumulation of visceral fat) and accumulated visceral fat-reducing agents comprising this substance as their active ingredient, as well as general processed food products, including specialty health food products (functional food products) having anti-obese and accumulated visceral fat-reducing functions and feed having these anti-obese and accumulated visceral fat-reducing activities comprising this substance as their active ingredient.

The present inventors repeatedly performed intense research in order to accomplish the above-mentioned object and as a result, they completed the present invention upon discovering that the above-mentioned object can be achieved by the following:

That is, the present invention has the following basic structure:

(1) Substances comprising:
components of coupling isomerized highly unsaturated fatty acids and/or derivatives thereof having an activity of specifically accelerating the uncoupling respiration of mitochondria (MC) and proton leak in the MC inner membrane in cells of the main tissues producing nonshivering thermogenesis (nST), skeletal muscles, white adipose tissue (WAT), brown adipose tissue (BAT), etc. of mammals including humans, and birds.

(2) The substances according to above-mentioned (1), wherein the components having the above-mentioned activity are coupling isomerized highly unsaturated fatty acids (HUFA).

(3) The substances according to claim 1, wherein the components having the above-mentioned activity are furan HUFA derivatives of oxidation products of HUFA derivatives.

(4) The substances according to above-mentioned (1), (2), or (3), wherein the components specifically act on mitochondria-containing cells of skeletal muscles of the main nST tissues, white adipose tissue, brown adipose tissue, etc., and which have an activity of markedly increasing the amount of uncoupled protein homologs (UCP homologs) expressed in said cells.

(5) An anti-obese (inhibiting accumulation of visceral fat (particularly mesenteric fat)) and visceral (particularly mesenteric) fat-reducing agent, comprising as its active ingredient:
the substance that has an activity of specifically accelerating the uncoupling respiration or proton leak of mitochondria (MC) of cells in the main nST tissues, skeletal muscles, WAT and BAT, etc., defined in above-mentioned (1), (2), or (3).

(6) Food products having anti-obese (inhibiting accumulation of visceral fat (particularly mesenteric fat)) and visceral (particularly mesenteric) fat-reducing activities, comprising as their active ingredient:
the substance that has an activity of specifically accelerating the uncoupling respiration or proton leak of mitochondria (MC) of cells in the main nST tissues, skeletal muscles, WAT and BAT, etc., defined in above-mentioned (1), (2), or (3).

(7) Feed having anti-obese (inhibiting accumulation of visceral fat (particularly mesenteric fat)) and visceral (particularly mesenteric) fat-reducing activities, comprising as their active ingredient:
the substance that has an activity of specifically accelerating the uncoupling respiration or proton leak of mitochondria (MC) of cells in the main nST tissues, skeletal muscles, WAT and BAT, etc., defined in above-mentioned (1), (2), or (3).

The present invention will now be explained in further detail.

The substance having the effect of specifically accelerating proton leak of MC in nST tissue is a substance comprising coupling isomerized highly unsaturated fatty acids and/or derivatives of the same. The term substance used in the present invention means anything of combination, composition, mixture, etc., comprising the component, and also the component itself.

Moreover, the term coupling isomerized high unsaturated fatty acids means a highly unsaturated fatty acid that has been coupling isomerized by any means.

In addition, the above-mentioned substance of the present invention is not limited to synthetic products and can be a concentrate, extract, purified product, isolated product, processed product, etc., as long as it has the same function as coupling isomerized highly unsaturated fatty acids.

Specific examples are trivalent or higher unsaturated fatty acids (HUFA) and derivatives derived from nature, including highly unsaturated fatty acids, such as α-linolenic acid, γ-linolenic acid, bis-homo-γ-linolenic acid, arachidonic acid, eicosapentaenoic acid, docosahexoenic acid, etc., and their mixtures, triacylglycerol, diacylglycerol, and monoacylglycerol wherein at least one of acyl group is a residue of HUFA and their mixtures, and glycerophospholipids, where at least one of acyl group is a residue of HUFA and their mixtures, such as the plasmologen-type phospholipids of phosphatidyl choline, phosphatidyl ethanolamine, phosphatidyl serine, phosphatidyl inositol, phosphatidyl glycerols, cardiolipin, phosphatidic acid, bis-phosphatidic acid, pyrophosphatic acid, ethanolamine plasmologen, etc., lyso-type phospholipids, such as lysolecithin, lysophosphatidyl ethanolamine, etc., sphingophospholipid s, such as myelin, seramide phosphoethanolamine, etc., and the like and mixtures of the same, safe HUFA salts, such as sodium, potassium, calcium, etc., esters of safe HUFA of fatty acid alcohols, such as methyl, ethyl, butyl, etc., and their mixtures, esters of safe HUFA of monosaccharides, such as glucose, etc., disaccharides, such as sucrose, etc., and oligosaccharides, such as xylitol, etc., and their mixtures, etc., that have been coupling isomerized by any means and substances with the same effects.

The term coupling isomerized highly unsaturated fatty acid in the present invention specifically means, for instance, coupled HUFA and/or their mixed fatty acids, HUFA and their mixtures-binding-typed coupled triacyl glycerol, for instance, coupled fish oil and coupled flaxseed oil, etc., 1- and/or 3-coupled HUFA and their mixtures-binding-type diacylglycerol, 1- and/or 2-coupled HUFA and their mixtures-binding-type diacylglycerol, 1- and/or 2-coupled HUFA and their mixtures-binding-type monoacylglycerol, 1- and/or 2-coupled HUFA and their mixtures-binding-type glycerophospholipid, such as 1- and/or 2-coupled HUFA and their mixtures-binding-type phosphatidylcholine, etc., coupled HUFA and their mixtures-substituted lysolecithin, etc., sodium salts, etc., of coupled HUFA and their mixtures, ethyl esters, etc., of coupled HUFA and their mixtures, sucrose esters, etc., of coupled HUFA and their mixtures, etc.

Ideal examples of the starting materials for the above-mentioned substance of the present invention are natural fats, particularly highly unsaturated oils and fats present in nature, such as marine oil and fats, including fish oils, etc., natural vegetable oils and fats, such as linseed oil, shiso oil, etc., flaxseed oil, linseed oil, perilla oil, rapeseed oil, oiticica oil, walnut oil, poppy oil, pomegranate oil, soybean oil, tung oil, evening primrose oil, gomukaku oil, limeseed oil, abura nataneshiyu, flaxseed oil, tall oil, balsam oil, sardine oil, eel oil, skipjack oil, salmon oil, salmon egg oil, mackerel oil, Pacific saury oil, herring oil, yellowtail oil, saurel oil, bluefin tuna oil, trout oil, trout egg oil, menhaden oil, jack mackerel oil, shark liver oil, cuttlefish liver oil, sardine liver oil, swordfish liver oil, skipjack liver oil, pollack liver oil, codfish liver oil, herring liver oil, saurel liver oil, seal oil, sea lion oil, various whale oils, etc. However, they are not limited to these and any starting material can be used as long as they are the same or similar to the above-mentioned substances.

Examples of the method of coupling isomerization of the above-mentioned materials are chemical treatment methods, lumen bacteria fermentation methods, laboratory animal intestinal flora fermentation methods, dehydrogenase treatment methods, and metal catalyst methods, such as the method of heating in the presence of sodium and potassium hydroxide by which coupling this HUFA and its alkali salt is obtained, the method of heating in the presence of sodium or potassium t-butyl alkoxide by which this HUFA glyceride and coupled isomer are obtained, the method of coupling isomerization of HUFA and its derivative by a lumen bacteria of a ruminant, such as Butyrivibrio fibrisolvens and harmless intestinal flora of another animals, the method of coupling isomerization that uses enzyme reaction, in vivo reaction, or biochemical reaction of cellular function, genetic function, etc., the method of heat treatment using palladium, titanium, zirconium, magnesium, and their alloys, Mg2Ni, LaNi5, TiFe, etc., which readily form a hydride, as the catalyst. However, this method is not limited to these and any method can be used as long as it is an effective coupling isomerization method.

Furthermore, double bond-position isomers and various stereoisomers (cis and trans) are included among the coupling isomers of these HUFA derivatives and, in light of the fact that it is very difficult to identify their structure and quantitatively determine the amount produced, it was decided that the coupling isomer in the present invention would be quantitatively determined by quantitative determination of all coupled double bonds.

Moreover, the derivative of the coupling isomerized highly unsaturated fatty acid of the present invention is not limited to synthetic products and can also be a natural product or processed product, as long as it is a derivative with the same functions as the above-mentioned highly unsaturated fatty acids. Specific examples are furan acid derivatives of in vivo and exogenous oxidation products, including polyvalent unsaturated fatty acids, coupled linoleic acid and its mixtures (hereafter referred to as CLA), salts, such as sodium salts, etc., esters, such as ethyl esters, etc., triacylglycerols, diacylglycerols, and monoacylglycerols where at least one of acyl group is CLA residue and their mixtures, glycerophospholipids where at least one of acyl group is CLA residue and their mixtures, and derivatives of the above-mentioned coupling isomerized HUFA and their mixtures, such as free acids, salts, esters, acylglycerols and their mixtures, glycerophospholipids and their mixtures, etc. For instance, endogenous furan acid derivatives from the fresh testicles of Hokkaido autumn salmon are mixtures of 6 types of isomers, as shown in Table 6, and exogenous furan acid obtained by auto-oxidation of CLA, the coupled fatty acid with the simplest structure, comprises several types of isomers similar to those in Table 6 (M. P. Yurawecz et al., Lipids, 30 (7), 595–598 (1995)).

Coupled FUFA are known to have anti-oxidation activity. They easily oxidize to produce furan derivatives and furan fatty acids are widely distributed in animals, including humans, and fish, plants, etc. (M. P. Yurawecz et al., Lipids, 30 (7), 595–598 (1995)). In particular, it is confirmed that furan fatty acids are present in very high concentrations of more than half the total hepatic and testicular lipids of fish, depending on the season. Furthermore, it is confirmed that furan fatty acids are contained in blood by absorption from the small intestine when administered to rats (D. M. Sand et al., Biochim Biophys Acta 751, 455–461 (1983)). The furan fatty acids contained in fish testicles is at its highest content immediately before the oviposition period in females and thereafter quickly disappears (D. M. Sand et al., Biochim Biophys Acta 793, 429–434 (1984)). There are reports relating to physiological effects of these furan fatty acids, such as prevention of cellular damage by peroxides, etc., (M. P. Yurawecz, INFORM 7(2), 156 (1996)).

The auto-oxidation product of furan fatty acids has an impeding effect on bacteria urease (G. Rosenblat et al., J Am Oil Chem Soc, 70, 501–505, (1993) and displays a physiological effect on products of oxidation by lipoxygenase-1 (R. F. Boyer et al., Chem Phys Lipids, 25, 237–246 (1979)).

The above-mentioned substance of the present invention is used as, for instance, the active ingredient of medical drugs, food, feed, etc., and therefore, it should be purified to the appropriate level in accordance with the purpose for which it is used. Relatively pure products can be used in processed foods, such as specialty health foods (functional foods) and when used in feed, etc., crude products can be used because the starting material is a natural oil and fat, such as sardine oil, linseed oil, perilla oil, rapeseed oil, manheden oil, cuttlefish liver oil, skipjack liver oil, etc.

The above-mentioned substance of the present invention is a substance comprising the above-mentioned coupling isomerized highly unsaturated fatty acid and can be for instance, coupled skipjack liver oil, coupled bluefin tuna oil, coupled salmon egg oil, coupled rapeseed oil, coupled tung oil, coupled soybean oil, coupled perilla coil, etc. The fact that, these are not edible oils as is and they are different from edible oil is clear because their effects are not observed with conventional edible oils, such as palm oil, coconut oil, lard, beef tallow, etc.

In order to clarify the utility of the above-mentioned active ingredient of the present invention, coupling isomerized fish oils were administered to morbid mice and coupling isomerized DHA binding-type fish oils and furan acid binding-type specialty fish oil, that is, the oxidation product of the typical DHA coupled isomer of 3HUFA, were each administered to the appropriate laboratory animals and the amount of visceral fat and UCP as well as UCP mRNA were determined, as will be described in specific terms in the examples that follow.

As a result, furfurylated oils and fats (containing furan fatty acids) and coupling isomerized DHA-bound neutral fats showed a significant amount of UCP expressed in BAT and little visceral (particularly mesenteric) fat in the control lard group (essential fatty acid-loaded).

With respect to the concentrations of mRNA of UCP subtypes expressed in the BAT of morbid mice administered coupling isomerized fish oil (in comparison to the control lard group), UCP-2 was expressed to a high concentration and UCP-1 and UCP-3 were expressed to a low concentration. When the general pattern of expression of each mRNA in the main nST tissues is first taken is taken into consideration using skeletal tissue (UCP-3 is expressed at a high concentration, while UCP-2 is expressed at an intermediate concentration and UCP-1 is not expressed), WAT (UCP-2 is expressed at a relatively high concentration, while UCP-3 is expressed at a low concentration and UCP-1 is not expressed), and BAT (UCP-1 is expressed at a high concentration and UCP-2 and UCP-3 are expressed at a low concentration), the concentration of UCP subtypes mRNA expressed in nST tissue of mice administered the active ingredient of the present invention appears to be UCP-2 expressed at a high concentration in BAT, UCP-2 expressed at a high concentration in WAT and UCP-3 expressed at a high concentration in skeletal muscles. It goes without saying that there was a significant drop in visceral (particularly mesenteric) fat of rats administered coupling isomerized DHA-bound fish oil with body weight, and this finding strongly supports the validity of the present hypothesis.

Expression of the UCP family is indispensable if the MC of cells in nST tissue are to burn fats and sugars. The active ingredient of the present invention has the effect of markedly increasing the amount of the UCP family expressed in cells of this tissue and this information on the molecular level in turn supports the fact that the active ingredient of the present invention is effective in inhibiting the visceral accumulation of fat and lowering accumulated visceral fat.

The above-mentioned active ingredient of the present invention has the effect of increasing the amount expressed of UCP homologs of inner membrane-penetrating proteins of MC in cells of nonshivering thermogenesis tissue, such as skeletal muscles, etc., involved in nST in mammals, including humans, and proton leak of MC in the above-mentioned cells. The above-mentioned substance of the present invention is a coupling isomer of HUFA derived from natural fat and furan acid, which is the oxidation product of the same isomer, as well as its derivatives, and as previously mentioned, is a high UCP-expressing substance that markedly increases the amount of UCP homolog expressed in the cells of nST tissue, such as skeletal muscles, etc. It can be identified and separated and purified using this expression activity as the indicator.

A visceral accumulated fat-lowering agent and visceral fat accumulation-inhibiting agent that is particularly effective against obesity can be prepared with the above-mentioned component of the present invention as its active ingredient. The carrier of this lowering agent or inhibiting agent can be an appropriate packing, binder, extender, disintegrating agent, surfactant, desiccant, filler, etc., depending on the form in which it is used. There are no special restrictions to the preparation form and it should be selected in accordance with the purpose for which it will used. Examples are solids, such as tablets, granules, powder, pills, capsules, etc., liquids, suspensions, emulsions, etc.

It is preferred that the visceral accumulated fat-lowering agent or visceral fat accumulation-inhibiting agent obtained in this way be orally administered. The dose is selected as needed in accordance with symptoms, etc., of the patient to be treated. Consequently, there are no special restrictions to the dose, number of times administered, etc.

Moreover, ordinary food products or specialty health food products (functional food products) can be prepared with the above-mentioned substance of the present invention as the active ingredient. Moreover, this substance can also be used as the additive for a variety of food products. With respect to the type of above-mentioned food product, the present invention can be used not only in specialty health food products, but also in ordinary health food products and food products that originally promote obesity, for instance, cakes, candies, chocolate, Japanese confectionery, meat products, ice cream, fish products, pre-prepared food products, etc.

The amount, form, etc., in which the above-mentioned substance of the present invention is added to the above-mentioned food products is selected as needed in accordance with the type of food product, product concept, product form, etc. It is usually preferred that it be added to the food product to a level that makes it possible to ingest 100 to 1,000 mg/time.

Furthermore, feed with visceral fat accumulating-inhibiting activity or visceral accumulated fat-lowering activity for domestic animals, etc., can be prepared by mixing the above-mentioned substance of the present invention with feed.

Ideal examples of feed to which the above-mentioned substance of the present invention is added are feed for domestic animals, such as cows, pigs, chickens, etc., and feed for domestic animals, such as meat-eating cows, etc., is a particularly ideal example. The amount, form, etc., in which the above-mentioned substance of the present invention is added to feed is determined as needed in accordance with the type of feed, rearing status of the domestic animal, etc. For instance, it is preferred that 50 to 500 mg be added to feed for rearing meat-eating cows.

BEST MODE FOR CARRYING OUT THE INVENTION

The present invention will now be explained in specific terms based on examples, but the present invention is not limited to these examples. Furthermore, almost the same results were obtained when the same experiments were performed on substances comprising coupling isomerized highly unsaturated fatty acids and/or their derivatives other than the above-mentioned.

EXAMPLE 1

1. Preparation of Samples
(1) Preparation of Coupling Isomerization Product of Triglycerides with High DHA Content DHA-highly containing triglyceride (TG) with a DHA content of as high as 45 to 50% was purified and prepared using bluefin tune eye-socket oil as the starting material (hereafter referred to bluefin tuna purified TG). Dimethyl formamide was added to approximately 120 g bluefin tuna purified TG to bring the volume to 200 ml. Next, the entire amount was transferred to a 500 ml Erlenmeyer flask with a stopper and approximately 12 g t-potassium butoxide (($CH_3$)$_3$)COK) were added to this. The air inside the flask was substituted with nitrogen and then it was incubated for 1 hour at 30° C.

After the incubation thereof, the solution was mad acidic and the reaction product was extracted with n-hexane. The extract was rinsed with water, dehydrated and then as much solvent as possible was removed under reduced pressure. The reaction product that was obtained was submitted to silicic acid column chromatography to prepare the coupling isomerized TG. Furthermore, the 20% diethyl ether fraction was recovered using n-hexane, n-hexane containing 5% diethyl ether, and n-hexane containing 20% diethyl ether as the solvents for the silicic acid column. The coupling isomerized TG obtained by this type of process accounted for 40 to 50% of the weight of the original oil and fat sample (bluefin tuna purified TG). The above-mentioned isomerization and purification were performed a total of 5 times to obtain approximately 250 g coupling isomerized TG.

(2) Quantitative Determination of Coupling Isomerized TG

The coupled acid content of TG obtained by the above-mentioned process was determined by conventional methods (Japan Oil Chemical Society, editors: Standard Oil and Fat Analysis Methods, 2.4.15–71). Ten to 20 mg oil and fat were precisely measured out in a 50 ml graduated flask. Once this had been brought to 50 ml with cyclohexane in a messflask, UV absorption was determined at 233 nm, 262 nm, 268 nm, 274 nm, 308 nm, 315 nm, and 322 nm and the coupled acid content was calculated in accordance with the following formula:

$$k\lambda = A\lambda/(b \times c)$$

($A$: absorbance at $\lambda$; $b$=cell length [cm]; $c$=concentration [g/l])

$$k_2 = k_{233} - K_0$$

$$k_3 = 2.8[k_{268} - \tfrac{1}{2}(k_{262} + k_{274})]$$

$$k_4 = 2.5[k_{315} - \tfrac{1}{2}(k_{308} + k_{322})]$$

In the case of esters, $k_0 = 0.07$.

The coupled diene, coupled triene and coupled tetraene content (%) are found from the following formulas:

$$\text{coupled diene} = 0.91\, k_2$$

$$\text{coupled triene} = 0.47\, k_3$$

$$\text{coupled tetraene} = 0.45\, k_4$$

When the coupled acid content of the sample oil (bluefin tuna purified TG) and isomerized TG was analyzed in accordance with the above-mentioned formula, the coupled diene content was 3.3% and the coupled triene and coupled tetraene content were both 0% with the sample oil. Moreover, the coupled diene content was 27.3%, the coupled triene content was 6.8%, and the coupled tetraene content was 4.4%, for a total coupled acid content of 38.3%, with the isomerized TG.

When reverse phase HPLC analysis of the above-mentioned coupling isomerized TG was performed, it was clear that the coupling isomer of DHA was the main fatty acid of the coupled unsaturated fatty acid. ODS (Nomura Kagaku, Develosil ODS-UG-5) was used as the column for HPLC and detection was performed by determining absorption at 235 nm using a UV detector.

Next, GC analysis of sample oil and coupling isomerized TG were performed. Analysis was performed at a column temperature of 200° C. using Omegawax 320 as the GC column. The results were a DHA content of sample oil of approximately 45%, with almost all of the highly unsaturated fatty acid being DHA. On the other hand, only approximately 2% DHA was detected from coupling isomerized TG and almost all of the DHA in the sample oil was isomerized one. The results were approximately the same as the results of the total amount of coupled acid by UV absorption (approximately 40%).

2. Laboratory Animals and Experimental Feed

After acclimation for 1 week on basic feed (F-2, Funabashi Farms Co., Ltd.) using 7-week-old Sprague-Dawley male rats, 7 rats per group were placed in the following 3 groups so that average body weight of each group would be the same and reared for 7 weeks. Rearing environment was adjusted to a temperature of 22 to 24° C. and humidity of 50 to 60%, with 12 hours of light and dark each (light time: 8:00 to 20:00, dark time: 20:00 to 8:00). Feed was supplied in restricted amounts and body weight was determined each week.

The basic composition of the feed used in the study is shown in Table 1. The components, including proteins, sugars, etc., were the same and the lipids were adjusted to 10% for each group. That is, the feed was prepared so that it comprised 1% ethyl linoleate as the essential fatty acid for each test group and 9% lard for the lard group, which was the control group, 2% bluefin tune purified TG (with the remainder being 7% lard) for the bluefin tuna refined TG group, and 2% coupling isomerized product of bluefin tune purified TG (with the remainder being 7% large) for the coupled acid group.

TABLE 1

| | Test group | | |
|---|---|---|---|
| | Lard group | Bluefin tuna purified TG group | Coupled acid group |
| Casein | 20.0% | 20.0% | 20.0% |
| Corn starch | 43.8% | 43.8% | 43.8% |
| Sucrose | 15.0% | 15.0% | 15.0% |
| Cellulose powder | 5.0% | 5.0% | 5.0% |
| Mixed Minerals ‡1 | 4.0% | 4.0% | 4.0% |
| Mixed vitamins ‡1 | 2.0% | 2.0% | 2.0% |
| Methionine | 0.2% | 0.2% | 0.2% |
| Ethyl linoleate | 1.0% | 1.0% | 1.0% |
| Lard | 9.0% | 7.0% | 7.0% |
| Bluefin tuna purified TG | | 2.0% | |
| Coupled acid ‡2 | | | 2.0% |

‡1: Made by Oriental Kobo Co., Ltd.
‡2: Coupling isomerization of bluefin tuna purified TG

3. Laboratory Animal Treatment Method and Analysis Method

After being reared for 7 weeks, the laboratory animals were fasted for 20 hours. The animals were sacrificed after performing laparoscopy under ether anesthetization and collecting blood from the inferior vena cava. Then mesenteric fat, perinephric fat, peritesticular fat, and interscapular brown fat were recovered and weighed and the brown fat was submitted to determinations of the amount of UCP. The plasma was obtained from blood by conventional methods and serum triglycerides, cholesterol, and phospholipid concentrations were determined. The amount of UCP was determined by the following method.

UCP protein extraction procedure:

Interscapular BAT extracted from rats was homogenized with 200 mM sucrose (comprising 10 mM Tris-HCl at pH of 7.5; 2 mM EDTA), centrifuged for 5 minutes at 3,100 rpm and 4° C. using a centrifugator on a cold table, and the supernatent thereof was further centrifuged for 10 minutes at 12,000 rpm and 4° C. The precipitate thus obtained (mitochondria fraction) was served as the sample.

Electrophoresis and western blotting:

Polyacrylamide gel electrophoresis was performed with 11% separated gel, and 50 μg sample protein were submitted to analysis from each lane. As the electrophoresis conditions, migration for 10 minutes at 100 V and then for 1 hour at 200 V were adopted. Transfer to the film (Hybond-C, Amersham) was performed for 30 minutes at 135 mA (2.5 mA/cm$^2$) by the semi-dry method. The film was blocked by immersion thereof for 1 hour or longer in 1% skim milk solution. Then the film was reacted with rabbit antibody (primary antibody diluted 3,000-times) to rat UCP, rinsed, and further reacted with rabbit IgG-peroxidase label (secondary antibody). After rinsing, the UCP band was detected on X-ray film with a chemiluminescence method detection reagent (Dupont). The darkness of the band on the film was read with a scanner and digitized by a computer.

4. Results

The UCP assuming that that of the control lard group was 100 and each of the other determinations of each test group are shown in Table 2. Even though there was not a difference between each test group in terms of the amount of feed ingested, body weight before and after rearing was significantly lower in the bluefin tuna purified TG group and coupled acid (coupling isomer of bluefin tuna purified TG) group when compared to the control lard group. Symptoms such as loose stools, diarrhea, etc., were not seen and there was not a difference in fecal output of each test group throughout the rearing period.

The amount of UCP increased by 1.5-times the control lard group in the bluefin tuna purified TG group and by approximately 2.0-times the control in the coupled acid group. Moreover, there was a tendency toward the total amount of mesenteric fat and intra-abdominal fat, which was the total of mesenteric fat, peritesticular fat, and perinephric fat, per weight being significantly less in the coupled acid group, and also less in the bluefin tuna purified TG group, than the control lard group. Furthermore, the plasma lipid concentration, such as tiglycerides, etc., showed a tendency toward being significantly lower or lower in the coupled acid group and the bluefin tuna purified TG group than the lard group.

It was clear that the effect of increasing UCP expression in BAT and inhibiting accumulation of visceral fat was seen with DHA-highly containing bluefin tuna purified TG (coupled acid content of 3.3%) and that this effect is marked with coupling isomerized oil (coupled acid content of 38.3%) that was prepared using this purified TG as the starting material.

TABLE 2

|  | Lard group | Bluefin tuna purified TG group | Coupled acid group |
| --- | --- | --- | --- |
| Body weight (g) | 520.4 ± 30.0 b | 495.7 ± 15.4 a | 477.4 ± 17.3 a* |
| Amount of feed ingested (%) | 1059 ± 78 | 1032 ± 54 | 1036 ± 28 |
| Mesenteric fat per body weight (%) | 1.08 ± 0.20 b | 1.00 ± 0.19 ab | 0.79 ± 0.14 a |
| Total intra-abdominal fat per body weight (%) | 5.43 ± 1.03 b | 4.54 ± 0.76 ab | 4.11 ± 0.96 a |
| Brown fat per body weight (%) | 0.077 ± 0.017 | 0.090 ± 0.020 | 0.069 ± 0.013 |
| UCP | 100 ± 9 b | 151 ± 18 a | 198 ± 21 c* |
| Plasma triglycerides (mg/dL) | 113.8 ± 31.6 b | 61.5 ± 16.7 a* | 72.0 ± 27.5 a |
| Plasma total cholesterol (mg/dL) | 79.2 ± 24.6 | 51.7 ± 16.1 | 61.4 ± 17.6 |
| Plasma phospholipids (mg/dL) | 118.3 ± 32.1 b | 86.0 ± 16.5 ab | 98.7 ± 25.4 ab |
| Total plasma lipids (mg/dL) | 311.2 ± 68.5 b | 199.2 ± 41.3 a* | 232.1 ± 64.9 ab |

The Figures represent the average±standard deviation.

Total intra-abdominal fat: Total of mesenteric fat, peritesticular fat, and perinephric fat.

UCP: represented by the relative when the control lard group was 100.

Coupled acid group: Coupling isomerization product of bluefin tuna purified TG

There is a statistically significant difference between characters that do not have the symbol ($p<0.05$, *$P<0.01$)

EXAMPLE 2

Determination of the amount of UCP subtypes expressed in BAT by ingestion of coupling isomerized fish oil and evaluation of the same In the past it was thought that UCP was specifically present on the mitochondria inner membrane of BAT and that it was responsible for thermogenesis in BAT. However, UCP-2 and UCP-3, which are thought to have strong homology with the conventional UCP (hereafter referred to as UCP-1) and the same function, were discovered in succession in the middle of last year (1997) and it was clear that they formed a family, as previously mentioned. The fact that expression of the UCP family is induced by a cold environment and eating has been previously reported, but the details of the same with respect to UCP-2 and UCP-3 are not clear.

In order to clarify accelerated expression of which UCP subtype by coupling isomerized HUFA-containing fish oil is responsible for acceleration of nST function, which was clarified in Example 1, the same coupling isomerized fish oil as in Example 1 was administered to C57BL mice, in which diet-induced obesity easily develops, and the concentration of genes of each subtype of UCP homolog expressed was quantitatively determined by Northern blotting analysis of Kawada et al. (Biochem. J., 293, 807–812, 1993).

The rearing conditions and diet conditions of the mice are shown in Table 3.

Rearing conditions: Eight-week-old C57BL/6 mice (male) were divided into 3 groups of 8 mice/group and acclimated with basic feed for 1 week. They were then reared (pair-feeding) for 5 weeks up to 14 weeks of age.

Dietary conditions: Food comprising only oleic acid (low-fat diet) served as the control diet (low-fat diet) and food to which lard or coupling isomerized fish oil had been added further served as the lard diet and the coupling isomerized fish oil diet (high-fat diets).

TABLE 3

| | Feed composition (g/100 g diet) | | |
|---|---|---|---|
| | Low-fat diet group | Lard group (high-fat diet) | Coupling isomerized fish oil group (high-fat diet) |
| Casein | 20 | 27.1 | 27.1 |
| α-Corn starch | 58.2 | 28.1 | 28.1 |
| Sucrose | 10 | 10 | 10 |
| Minerals | 3.5 | 3.5 | 3.5 |
| Cellulose | 5 | 5 | 5 |
| Vitamins | 1 | 1 | 1 |
| D, L-methionine | 0.3 | 0.3 | 0.3 |
| Oleic acid | 2 | 2 | 2 |
| Lard | — | 23 | — |
| Coupling isomerized fish oil | — | — | 23 |

Figure 1:
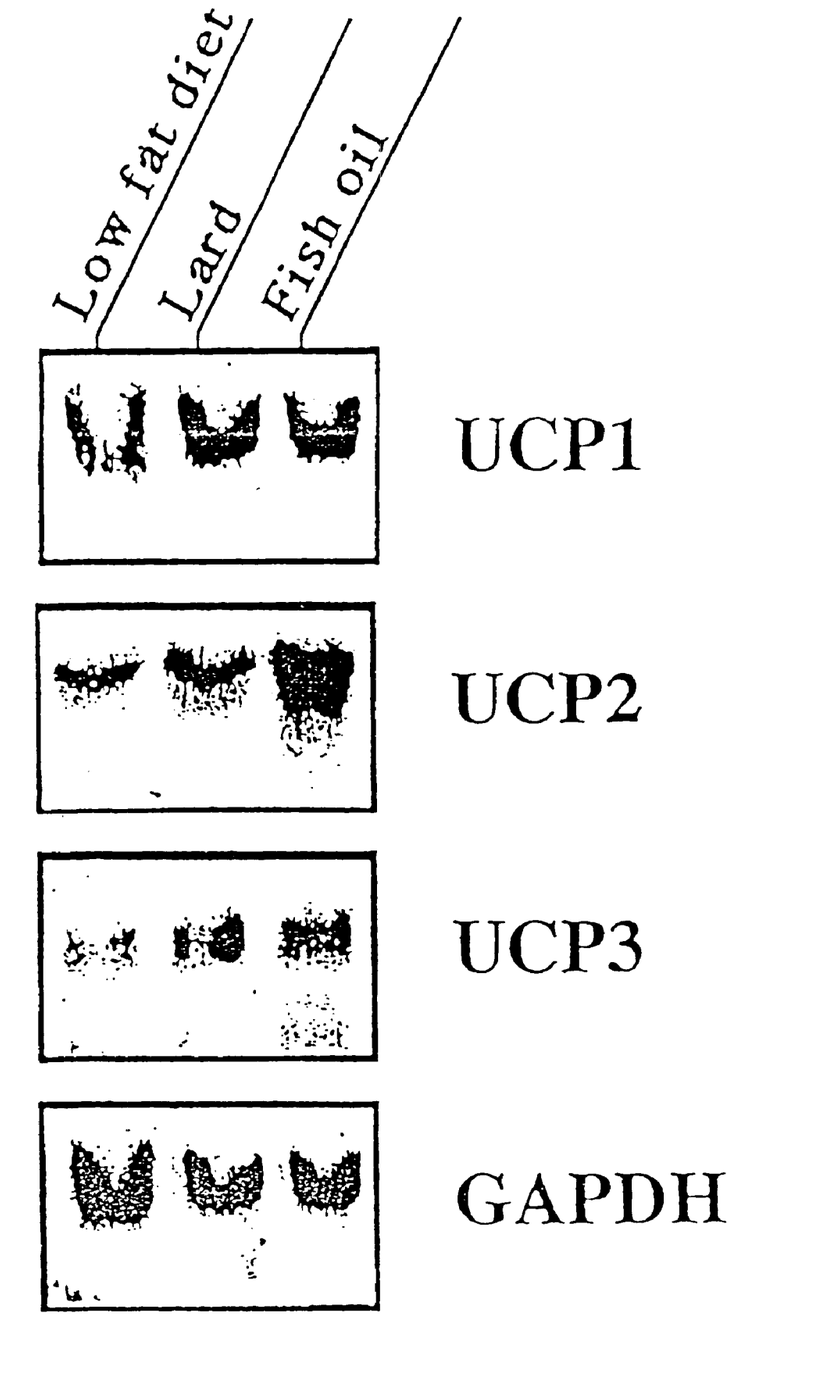
FIG. 1 shows the mRNA concentration of UCP homologs expressed in interscapular BAT.

The results of determining body weight and the amount of accumulated fat, etc., are shown in Table 4. As a result, the weight of perinephric adipose tissue, adipose tissue around the seminal glands, and mesenteric adipose tissue decreased significantly with the coupling isomerized fish oil diet when compared to the lard diet. Moreover, it is particularly significant that the results of this coupling isomerized fish oil rivaled those with the low-fat diet (weight ratio of 2%). In order to analyze the mechanism of the effects of this coupling isomerized fish oil, comparative tests were conducted on the amount of mRNA of each subtype of the UCP family (UCP-1, -2, and -3) expressed in BAT. The results are shown in FIG. 1. GAPDH was used here as the internal standard gene for mRNA analysis. As is clear from FIG. 1, expression of UCP-2 gene increased markedly with the coupling isomerized fish oil diet. According to past knowledge, the increase in UCP expression is inhibited by the noradrenaline that is secreted from the sympathetic nerve terminals that support BAT and it is clear that this mainly leads to an increase in UCP-1. As previously mentioned, the coupling isomerized fish oil in the present experiment was evaluated to have specifically enhanced the UCP-2 gene and it was therefore concluded that rather than the coupling isomerized fish oil acting to accelerate the function of BAT via the sympathetic nervous system, the coupling isomerized fish oil component acts directly on the BAT.

UCP-2 differs from UCP-1 in that it is widely distributed not only in BAT, but also in the main nST tissues, such as WAT and skeletal muscles, and therefore, coupling isomerized HUFA derivatives (of fish oil) are very effective against obesity in humans.

TABLE 4

Effect of oils and fats on mouse adipose tissue weight and body weight

| | Low-fat diet group | Lard group (high-fat diet) | Coupling isomerized fish oil group (high-fat diet) |
|---|---|---|---|
| Body weight (g) | 25.7 ± 0.43 | 26.7 ± 0.60 | 26.1 ± 0.26 |
| Amount of feed ingested (kcal) | 541.3 ± 10.7 | 541.9 ± 14.5 | 540.0 ± 8.5 |
| Perinephric WAT (g/100 g body weight) | 0.81 ± 0.06 a | 1.01 ± 0.07 b | 0.72 ± 0.05 a |
| Seminal vesicle WAT (g/100 g body weight) | 1.89 ± 0.06 a | 2.35 ± 0.09 b | 1.44 ± 0.07 c |
| Mesenteric WAT (g/100 g body weight) | 0.97 ± 0.06 a | 1.25 ± 0.07 b | 0.94 ± 0.05 a |
| Interscapular BAT (g/100 g body weight) | 0.96 ± 0.06 | 1.12 ± 0.06 | 1.14 ± 0.05 |

The numbers show the average±standard deviation (8 animals)

There is a statistically significant difference between figures on the same line with different superscripts (p<0.01).

EXAMPLE 3

1. Preparation of Samples (1) Preparation of Coupling Isomerization Product of DHA Ethyl Ester Eighty milliliters dimethylformamide were added to 100 g DHA ethyl ester (99% Harima Kasei) and 31.5 g (equimolar amount in terms of DHA ethyl ester) potassium t-butoxide (($CH_3)_3$ C—OK) were further added thereof. The total amount was transferred to a 500 ml Erlenmyer flask with a stopper and the air inside the flask was substituted with nitrogen, and then it was incubated for 1 hour at 30° C.

After the incubation thereof, the reaction solution was made acidic with 2 N hydrochloric acid and extracted with n-hexane. The extract was rinsed with water and dehydrated and as much solvent as possible was distilled off under reduced pressure. The concentrate thus obtained (reaction product) was submitted to silicic acid column chromatography to prepare the coupling isomerized DHA triglyceride.

Furthermore, 20% diethyl ether fractions were recovered using n-hexane, n-hexane containing 5% diethyl ether, and n-hexane containing 20% diethyl ether. The yield of coupling isomerized DHA ethyl ester obtained by this type of procedure was 49%.

(2) Quantitative Determination of Coupling Isomerized DHA Ethyl Ester

The coupling isomerized acid content of ethyl ester obtained by the above-mentioned procedure was determined by conventional methods as in Example 1.

It is clear that the coupling isomerized acid content of the starting DHA ethyl ester and its isomerized ethyl ester was 0% coupled diene, coupled triene, and coupled tetraene in the starting DHA ethyl ester, but 83.0% coupled diene, 9.7% coupled triene, and 7.0% coupled tetraene in the isomerized ester, with the entire amount of DHA (99% or more) being coupling isomerized.

Furthermore, reverse-phase HPLC (column: ODS (Nomura Kagaku, Develosil ODS-UG-5) analysis of the DHA ethyl ester and its coupling isomerized DHA ethyl ester starting materials was performed and it was confirmed that the fatty acid of DHA ethyl ester is DHA and only a single peak is detected with the isomerized ethyl ester and therefore, the DHA in the DHA ethyl ester is all but completely coupling isomerized. Furthermore, the results of determining the amount of coupling acid by UV absorption coincided (almost 100%).

2. Laboratory Animals and Experimental Feed

1) Laboratory Animals and Rearing Method
These were the same as in Example 1.
2) Experimental Feed With the exception that 8.5% lard was added to 0.5% starting DHA ethyl ester and served as the control group, and 8.5% lard was added to 0.5% coupled DHA ethyl ester and served as the coupled DHA ethyl group, the feed was in accordance with Example 1.

3. Laboratory Animal Treatment Method and Analysis Method

After being reared for 7 weeks, the animals were fasted for 20 hours and then sacrificed after performing laparoscopy under ether anesthetization and collecting blood from the inferior vena cava. Then the mesenteric fat, perinephric fat, peritesticular fat, and interscapular brown fat were collected and weight was determined, and the brown fat was submitted to determinations of the amount of UCP.

Determination of the amount of UCP was performed as in Example 1.

4. Results

The UCP assuming that that of the control group is 100 and each of the other determinations of each of the test groups are shown in Table 5. Even though there was not a difference in the amount of feed ingested between the test groups, body weight after rearing was significantly lower in the coupled acid group (coupled isomerization product of DHA ethyl) when compared to the control group. Symptoms of loose stools, diarrhea, etc., were not seen in any test group and there were no difference in fecal output throughout the rearing period.

The amount of UCP of the coupling isomerized DHA ethyl increased approximately 1.8-times when compared to the control group. Mesenteric fat and the total amount of intra-abdominal fat of the combined mesenteric fat, peritesticular fat, and perinephric fat, per body weight was significantly lower with the coupled acid ethyl group when compared to the control group, indicating that the coupling isomerized DHA ethyl ester displays intra-abdominal fat, particularly, mesenteric fat, accumulation-inhibiting and mesenteric accumulated fat-lowering activities by increasing the amount of UCP expressed.

TABLE 5

|  | Control group | Coupled acid ethyl group |
| --- | --- | --- |
| Body weight (g) | 515.8 ± 29 b | 465.3 ± 19.5 a‡ |
| Amount of feed ingested (g) | 1041 ± 67 | 1035 ± 36 |
| Mesenteric fat per body weight (%) | 1.01 ± 0.20 b | 0.75 ± 0.16 a |
| Total intra-abdominal fat per body weight (%) | 5.29 ± 0.93 b | 4.15 ± 0.73 a |
| Brown fat per body weight (%) | 0.073 ± 0.015 | 0.075 ± 0.014 |
| UCP | 100 ± 8 | 178 ± 16 a‡ |

The figures represent the average±standard deviation.
Total intra-abdominal fat: Total of mesenteric fat, peritesticular fat, perinephric fat.

UCP: represented by the relative when the control lard group was 100.

There is a statistically significant difference between characters that do not have the same symbol (p<0.05, *P<0.01).

EXAMPLE 4

1. Preparation of Samples (1) Preparation and Analysis of Furanoid Fatty Acid (Hereafter F Acid) Ethyl Esters Fresh roe (testicles) of Hokkaido autumn salmon (Oncorhynchus keta) were freeze dried and then thoroughly crushed with a mixer. The crushed product was soaked in ethanol and then shook and the undissolved matter was filtered to obtain the ethanol extract.

The ethanol was distilled off the extract with an evaporator to obtain an oily lipid fraction (yield of 2.5%). This oil was submitted to silicic acid column chromatography. The F acid triglyceride fraction was separated by the same procedure as in Example 1.

This fraction was ethyl esterified using an acid catalyst in accordance with conventional methods and passed through the same column as previously described to obtain the purified ester. This ester was dissolved in acetonitrile and submitted to reverse-phase HPLC (column: Zorbax ODS (Nomura Kagaku) in accordance with the method of Ota et al. (Chromatography, 15, No. 4, 250–253 (1994)) to obtain an F acid ethyl ester mixture. F acid triglyceride was separately methyl esterified by conventional methods for the purpose of submission to analysis and the F acid was identified in accordance with the method of Ota et al.

As a result, the furan acid composition (molar %) of this ethyl ester was 59% F6, 20% F4, 13% F5, 6% F2, and 2% F8 in accordance with the structure of furanoid fatty acids in chemical formula 1 and Table 6.

Chemical formula 1

TABLE 6

Structure of furanoid fatty acids

|  | m | n | $R_1$ | $R_2$ |
|---|---|---|---|---|
| $F_0$ | 4 | 6 | $CH_3$ | $CH_3$ |
| $F_1$ | 2 | 8 | $CH_3$ | $CH_3$ |
| $F_2$ | 4 | 8 | H | $CH_3$ |
| $F_3$ | 4 | 8 | $CH_3$ | $CH_3$ |
| $F_4$ | 2 | 10 | $CH_3$ | $CH_3$ |
| $F_5$ | 4 | 10 | H | $CH_3$ |
| $F_6$ | 4 | 10 | $CH_3$ | $CH_3$ |
| $F_7$ | 4 | 12 | H | $CH_3$ |
| $F_8$ | 4 | 12 | $CH_3$ | $CH_3$ |
| $F_{2'}$ | 2 | 10 | H | $CH_3$ |
| $F_{6'}$ | 2 | 12 | $CH_3$ | $CH_3$ |

(2) Production of Auto-oxidation Product of F Acids and their Structure

It is a known fact that F acid methyl esters readily auto-oxidize and change to the corresponding unsaturated F acid methyl ester via dioxo-enoate (G. Rosenblat et al., J Am Oil Chem Soc, 70 (5), 501–505 (1993)).

This F acid ethyl ester was analyzed in accordance with the method of Rosenblat et al., and it was concluded that it contains approximately 8% of a similar auto-oxidation product.

2. Laboratory Animals and Experimental Feed
1) Laboratory Animals and Rearing Method
   These were the same as in Example 1.
2) Experimental Feed
   With the exception that 8.5% lard was added to 0.5% F acid ethyl ester and served as the F acid ethyl group, the experimental feed was in accordance with Example 1.

3. Laboratory Animal Treatment Method and Analysis Method

These were the same as in Example 3.

4. Results

The UCP assuming that that of the control group was 100 and other determinations are shown in Table 7. Even though there was no difference in the amount of feed ingested, body weight after rearing was significantly lower in the F acid ethyl group when compared to the control group.

Symptoms such as loose stools, diarrhea, etc., were not seen and there was not a difference in fecal output of any group throughout the rearing period.

The amount of UCP expressed increased by approximately 3-times or less in the F acid ethyl ester group when compared to the control group. Moreover, the ratio of mesenteric fat and intra-abdominal fat (total of mesenteric fat, peritesticular fat and perinephric fat) per body weight was significantly smaller in the F acid ethyl ester group than the control group. This indicates that the F acid ethyl ester accelerates intra-abdominal fat, to say nothing of mesenteric fat, accumulation-inhibiting and mesenteric accumulated fat-lowering activities by markedly increasing the amount of UCP expressed.

TABLE 7

|  | Lard group (control group) | F acid ethyl [ester] group |
|---|---|---|
| Body weight (g) | 519.3 ± 29 b | 461 ± 18.1 a‡ |
| Amount of feed ingested (g) | 1051 ± 75 | 1043 ± 29 |
| Mesenteric fat per body weight (%) | 1.01 ± 0.19 b | 0.71 ± 0.13 a |
| Total intra-abdominal fat per body weight (%) | 5.49 ± 1.05 b | 3.71 ± 0.83 a |
| Brown fat per body weight (%) | 0.081 ± 0.015 | 0.090 ± 0.019 |
| UCP | 100 ± 11 b | 291 ± 25 a‡ |

The figures represent the average±standard deviation.
Total Intra-abdominal fat: Total of mesenteric fat, peritesticular fat, perinephric fat.
UCP: represented by the relative when the control lard group was 100.
There is a satistically significant difference between characters that do not have the same symbol ($p<0.05$, *$P<0.01$).

EXAMPLE 5

1. Preparation of Samples
1) Preparation and Analysis of Coupling Isomerization Product of α-linoleic Acid Ethyl Ester A coupling isomerization product was prepared from α-linoleic acid ethyl ester (Sigma) by the same method as in Example 3. It was confirmed by UV absorption and HPLC analysis that coupling isomerization was all but complete.

2) Preparation and Analysis of Eicosapentaenoic Acid (EPA) Ethyl Ester

A coupling isomerization product was prepared from EPA ethyl ester (Sigma) by the same method as in Example 3. It was confirmed by UV absorption and HPLC analysis that coupling isomerization was all but complete.

2. Laboratory Animals and Experimental Feed
1) Laboratory Animals and Rearing Method
   These were the same as in Example 1.
2) Experimental Feed
   Other than the fact that 8% lard was added to 1.0% coupled α-linoleic acid ethyl ester and served as the coupled ALA ethyl ester group and similarly, 8% lard was added to 1.0% coupled EPA ethyl ester and served as the coupled EPA ethyl ester group, the feed was in accordance with Example 1.

3. Laboratory Animal Treatment Method and Analysis Method

These were the same as in Example 3.

4. Results

The UCP assuming that that of the lard control group was 100 and each of the other determinations are shown in Table 8. Even though there was not a difference between each test group in terms of the amount of feed ingested, body weight after rearing was significantly lower in both the coupled ALA ethyl ester group and the coupled EPA ethyl ester group when compared to the control group.

There were no symptoms such as loose stools, diarrhea, etc., and there was not a difference in fecal output in any of the groups throughout the rearing period.

The amount of UCP showed an increase of approximately 1.7-times the lard control group in the coupled ALA ethyl ester group and approximately 2.4-times the lard control group in the coupled EPA ethyl ester group. Moreover, when compared to the lard group, both coupled acid groups showed a significantly lower mesenteric fat and total intra-abdominal fat of combined mesenteric fat, peritesticular fat, and perinephric fat, per body weight. This indicates that both the α-linoleic acid ethyl ester and the EPA ethyl ester coupled isomerization product have the ability to inhibit accumulation of intra-abdominal fat, including mesenteric fat.

TABLE 8

|  | Lard group | Coupled ALA ethyl [ester] group | Coupled EPA ethyl [ester] group |
| --- | --- | --- | --- |
| Body weight (g) | 507.8 ± 12.4 a | 469.7 ± 16.4 b | 471.3 ± 20.5 b |
| Amount of feed ingested (g) | 994 ± 54 | 1022 ± 63 | 982 ± 38 |
| Mesenteric fat per body weight (%) | 0.98 ± 0.09 a | 0.65 ± 0.18 b | 0.68 ± 0.10 b |
| Total intra-abdominal fat per body weight (%) | 4.85 ± 0.64 a | 3.85 ± 0.56 b | 3.71 ± 0.48 b |
| Brown fat per body weight (%) | 0.088 ± 0.012 | 0.093 ± 0.021 | 0.079 ± 0.011 |
| UCP | 100 ± 11 a | 169 ± 19 b | 240 ± 27 c |

The figures represent the average±standard deviation.
Total Intra-abdominal fat: Total of mesenteric fat, peritesticular fat, perinephric fat.
UCP: represented by the relative when the control lard group was 100.
There is a satistically significant difference between characters that do not have the same symbol ($p<0.05$)

INDUSTRIAL APPLICABILITY

The above-mentioned substances obtained by the present invention have the ability to specifically accelerate the uncoupling respiration of MC of, for instance BA, mitochondria-containing cells and WA, etc., and proton leak of the MC inner membrane of skeletal muscles which are the main tissues involved in nST, WAT, BAT, etc. in mammals including humans, and birds. The present invention presents an anti-obese (inhibiting accumulation of visceral fat (particularly mesenteric fat)) and visceral (particularly mesenteric) fat-reducing agent, food products having anti-obese (inhibiting accumulation of visceral fat (particularly mesenteric fat)) and visceral (particularly mesenteric) fat-reducing activities comprising as their active ingredient the above-mentioned substance, and feed having anti-obese (inhibiting accumulation of visceral fat (particularly mesenteric fat)) and visceral (particularly mesenteric) fat-reducing activities comprising as their active ingredient the above-mentioned substance.

What is claimed is:

1. A method for inhibiting the accumulation of visceral fat in a mammal, comprising administering to the mammal a component of coupling at least one of isomerized highly unsaturated fatty acid or a derivative thereof, which has at least one activity of specifically accelerating the uncoupling respiration of mitochondria and accelerating proton leak in the mitochondrial inner membrane of one or more of a tissue of the mammal which produces nonshivering thermogenesis, skeletal muscle, white adipose tissue, and brown adipose tissue.

2. The method of claim 1, wherein the visceral fat is mesenteric fat.

3. The method of claim 1, wherein the component of coupling isomerized highly unsaturated fatty acid are coupled isomerized highly unsaturated fatty acids.

4. The method of claim 1, wherein the component of coupling isomerized highly unsaturated fatty acid is a furan highly unsaturated fatty acid derivatives obtained by oxidation of highly unsaturated fatty acid derivatives.

5. The method of claim 1, wherein the components have an activity of increasing the amount of uncoupling protein homologs expressed in the cells relative to the amount of uncoupling protein homologs in the cells in the absence of administering the components.

6. The method of claim 1, wherein the components of coupling isomerized highly unsaturated fatty acid specifically act on at least one of mitochondria-containing skeletal muscle cells of the tissues producing nonshivering thermogenesis, mitochondria-containing white adipose tissue cells, and mitochondria-containing brown adipose tissue cells; and wherein the components have an activity of increasing the amount of uncoupling protein homologs expressed in the cells relative to the amount of uncoupling protein homologs in the cells in the absence of administering the components.

7. The method of claim 6, wherein the components of coupling isomerized highly unsaturated fatty acid specifically act on mitochondria-containing skeletal muscle cells of the tissues producing nonshivering thermogenesis, mitochondria-containing white adipose tissue cells, and mitochondria-containing brown adipose tissue cells.

8. The method of claim 1, wherein the highly unsaturated fatty acid is dexosahexanoic acid containing triglyceride.

9. A method for reducing visceral fat in a mammal, comprising administering to the mammal a component of coupling at least one of isomerized highly unsaturated fatty acid or a derivative thereof, which has at least one activity of specifically accelerating the uncoupling respiration of mitochondria and accelerating proton leak in the mitochondrial inner membrane of one or more of a tissue of the mammal which produces nonshivering thermogenesis, skeletal muscle, white adipose tissue, and brown adipose tissue.

10. The method of claim 9, wherein the visceral fat is mesenteric fat.

11. The method of claim 9, wherein the component of coupling isomerized highly unsaturated fatty acid are coupled isomerized highly unsaturated fatty acids.

12. The method of claim 9, wherein the component of coupling isomerized highly unsaturated fatty acid is a furan highly unsaturated fatty acid derivatives obtained by oxidation of highly unsaturated fatty acid derivatives.

13. The method of claim 9, wherein the components have an activity of increasing the amount of uncoupling protein homologs expressed in the cells relative to the amount of uncoupling protein homologs in the cells in the absence of administering the components.

14. The method of claim 9, wherein the components of coupling isomerized highly unsaturated fatty acid specifically act on at least one of mitochondria-containing skeletal muscle cells of the tissues producing nonshivering thermogenesis, mitochondria-containing white adipose tissue cells, and mitochondria-containing brown adipose tissue cells; and wherein the components have an activity of increasing the amount of uncoupling protein homologs expressed in the cells relative to the amount of uncoupling protein homologs in the cells in the absence of administering the components.

15. The method of claim 14, wherein the components of coupling isomerized highly unsaturated fatty acid specifically act on mitochondria-containing skeletal muscle cells of the tissues producing nonshivering thermogenesis, mitochondria-containing white adipose tissue cells, and mitochondria-containing brown adipose tissue cells.

16. The method of claim 9, wherein the highly unsaturated fatty acid is dexosahexanoic acid containing triglyceride.

* * * * *